(12) United States Patent
Mickiewicz et al.

(10) Patent No.: US 11,207,107 B2
(45) Date of Patent: Dec. 28, 2021

(54) SYSTEMS AND METHODS FOR REDUCING THE RISK OF PROXIMAL JUNCTIONAL KYPHOSIS USING A BONE ANCHOR OR OTHER ATTACHMENT POINT

(71) Applicant: Medos International Sarl, Le Locle (CH)

(72) Inventors: Christopher Mickiewicz, Bridgewater, MA (US); Michael O'Neil, West Barnstable, MA (US); Randal Betz, Ocean City, NJ (US); Baron Lonner, New York, NY (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/584,528

(22) Filed: Sep. 26, 2019

(65) Prior Publication Data

US 2020/0015862 A1 Jan. 16, 2020

Related U.S. Application Data

(63) Continuation of application No. 15/663,856, filed on Jul. 31, 2017, now Pat. No. 10,463,403.

(51) Int. Cl.
*A61B 17/70* (2006.01)
*A61B 17/56* (2006.01)

(52) U.S. Cl.
CPC ...... *A61B 17/7049* (2013.01); *A61B 17/7034* (2013.01); *A61B 17/7041* (2013.01);
(Continued)

(58) Field of Classification Search
CPC ... A61B 17/7019–7031; A61B 17/7049–7053; A61B 17/7062–707; A61B 17/70–7031
See application file for complete search history.

(56) References Cited

U.S. PATENT DOCUMENTS

| 4,570,618 A | 2/1986 | Wu |
| 5,030,220 A | 7/1991 | Howland |

(Continued)

FOREIGN PATENT DOCUMENTS

| EP | 0928603 A1 | 7/1999 |
| EP | 1 205 152 B1 | 9/2004 |

(Continued)

OTHER PUBLICATIONS

U.S. Appl. No. 15/663,856, filed Jul. 31, 2017, Systems and Methods for Reducing the Risk of Proximal Junctional Kyphosis Using a Bone Anchor or Other Attachment Point.
(Continued)

*Primary Examiner* — Eduardo C Robert
*Assistant Examiner* — Michelle C Eckman
(74) *Attorney, Agent, or Firm* — Barnes & Thornburg LLP

(57) ABSTRACT

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a bone anchor implanted in a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct, thereby providing a more-gradual transition from the instrumented vertebrae to the natural patient anatomy adjacent thereto. The extension can be placed with little or no soft tissue disruption.

20 Claims, 8 Drawing Sheets

(52) U.S. Cl.
CPC ...... *A61B 17/7053* (2013.01); *A61B 17/7056* (2013.01); *A61B 17/7082* (2013.01); *A61B 17/7083* (2013.01); *A61B 17/7002* (2013.01); *A61B 17/7032* (2013.01); *A61B 2017/564* (2013.01)

(56) References Cited

U.S. PATENT DOCUMENTS

| | | | |
|---|---|---|---|
| 5,190,545 A | 3/1993 | Corsi et al. |
| 5,318,566 A | 6/1994 | Miller |
| 5,395,374 A | 3/1995 | Miller et al. |
| 5,415,658 A | 5/1995 | Kilpela et al. |
| 5,417,690 A | 5/1995 | Sennett et al. |
| 5,454,812 A | 10/1995 | Lin |
| 5,456,722 A | 10/1995 | McLeod et al. |
| 5,496,318 A | 3/1996 | Howland et al. |
| 5,540,698 A | 7/1996 | Preissman |
| 5,540,703 A | 7/1996 | Barker, Jr. et al. |
| 5,609,634 A | 3/1997 | Voydeville |
| 5,649,927 A | 7/1997 | Kilpela et al. |
| 5,702,399 A | 12/1997 | Kilpela et al. |
| 5,725,582 A | 3/1998 | Bevan et al. |
| 5,772,663 A | 6/1998 | Whiteside et al. |
| 5,782,831 A | 7/1998 | Sherman et al. |
| 5,899,903 A | 5/1999 | Cotrel |
| 6,086,590 A | 7/2000 | Margulies et al. |
| 6,099,527 A | 8/2000 | Hochschuler et al. |
| 6,277,120 B1 | 8/2001 | Lawson |
| 6,391,030 B1 | 5/2002 | Wagner et al. |
| 6,436,099 B1 | 8/2002 | Drewry et al. |
| 6,514,255 B1 | 2/2003 | Ferree |
| 6,605,091 B1 | 8/2003 | Iwanski |
| 6,946,000 B2 | 9/2005 | Senegas et al. |
| 7,087,083 B2 | 8/2006 | Pasquet et al. |
| 7,250,054 B2 | 7/2007 | Allen et al. |
| 7,666,208 B1 | 2/2010 | Asfora |
| 7,682,376 B2 | 3/2010 | Trieu |
| 7,717,938 B2 | 5/2010 | Kim et al. |
| 7,717,939 B2 | 5/2010 | Ludwig et al. |
| 8,177,810 B2 | 5/2012 | Ferree |
| 8,246,655 B2 | 8/2012 | Jackson et al. |
| 8,308,771 B2 | 11/2012 | Bennett et al. |
| 8,313,513 B2 | 11/2012 | Beger et al. |
| 8,333,791 B2 | 12/2012 | Carls et al. |
| 8,361,117 B2 | 1/2013 | Michielli et al. |
| 8,394,128 B2 | 3/2013 | Kothari et al. |
| 8,403,964 B2 | 3/2013 | Fielding et al. |
| 8,419,772 B2 | 4/2013 | Thompson et al. |
| 8,465,527 B2 | 6/2013 | Clement |
| 8,529,607 B2 | 9/2013 | Alamin et al. |
| 8,696,710 B2 | 4/2014 | Fielding et al. |
| 8,740,941 B2 | 6/2014 | Thramann |
| 8,758,409 B2 | 6/2014 | Hochschuler et al. |
| 8,758,411 B1 | 6/2014 | Rayon et al. |
| 8,845,689 B2 | 9/2014 | Douget et al. |
| 8,870,881 B2 | 10/2014 | Rezach et al. |
| 8,926,668 B2 | 1/2015 | Douget |
| 8,940,019 B2 | 1/2015 | Gordon et al. |
| 8,979,897 B2 | 3/2015 | Butterfield et al. |
| 8,979,899 B2 | 3/2015 | Ciupik et al. |
| 9,084,637 B2 | 7/2015 | Pasquet et al. |
| 9,144,440 B2 | 9/2015 | Aminian |
| 9,186,185 B2 | 11/2015 | Hestad et al. |
| 9,265,532 B2 | 2/2016 | Lamborne et al. |
| 9,295,496 B2 | 3/2016 | Le Couedic et al. |
| 9,295,499 B2 | 3/2016 | Alamin et al. |
| 9,314,275 B2 | 4/2016 | Clement et al. |
| 9,439,686 B2 | 9/2016 | Rooney et al. |
| 9,585,705 B2 | 3/2017 | Koch et al. |
| 9,668,773 B2 | 6/2017 | Alexander et al. |
| 9,675,386 B2 | 6/2017 | Akbarnia et al. |
| 9,770,268 B2 | 9/2017 | Albert et al. |
| 9,848,919 B2 | 12/2017 | Simpson et al. |
| 9,861,391 B2 | 1/2018 | Larroque-Lahitette |
| 9,901,377 B2 | 2/2018 | Legallois |
| 9,924,970 B2 | 3/2018 | Gordon |
| 9,924,976 B2 | 3/2018 | Simpson et al. |
| 9,949,778 B2 | 4/2018 | Baccelli et al. |
| 9,993,274 B2 | 6/2018 | Belliard |
| 10,034,692 B2 | 7/2018 | Palmer et al. |
| 10,098,673 B2 | 10/2018 | Rooney et al. |
| 10,456,174 B2 | 10/2019 | Mickiewicz et al. |
| 10,463,403 B2 | 11/2019 | Mickiewicz et al. |
| 10,512,486 B2 | 12/2019 | Larroque-Lahitette |
| 2004/0248078 A1 | 12/2004 | Manolagas et al. |
| 2005/0080420 A1 | 4/2005 | Farris et al. |
| 2005/0192581 A1 | 9/2005 | Molz et al. |
| 2005/0245929 A1 | 11/2005 | Winslow et al. |
| 2006/0241601 A1 | 10/2006 | Trautwein et al. |
| 2006/0247625 A1 | 11/2006 | Morrison et al. |
| 2007/0043365 A1 | 2/2007 | Ritland |
| 2007/0073293 A1 | 3/2007 | Martz et al. |
| 2007/0093823 A1 | 4/2007 | Booth et al. |
| 2007/0233089 A1 | 10/2007 | DiPoto et al. |
| 2007/0299445 A1 | 12/2007 | Shadduck et al. |
| 2008/0140133 A1 | 6/2008 | Allard et al. |
| 2008/0177326 A1 | 7/2008 | Thompson |
| 2008/0234744 A1* | 9/2008 | Zylber ............ A61B 17/7031 606/264 |
| 2008/0294199 A1 | 11/2008 | Kohm et al. |
| 2009/0149885 A1 | 6/2009 | Durward et al. |
| 2009/0177233 A1* | 7/2009 | Malek ............. A61B 17/7022 606/263 |
| 2009/0204151 A1 | 8/2009 | Bracken |
| 2009/0248081 A1 | 10/2009 | LeHuec et al. |
| 2009/0270918 A1 | 10/2009 | Attia et al. |
| 2010/0069961 A1 | 3/2010 | DiPoto et al. |
| 2010/0137913 A1 | 6/2010 | Khatchadourian et al. |
| 2010/0292736 A1 | 11/2010 | Schwab |
| 2010/0318133 A1* | 12/2010 | Tornier ............ A61B 17/7067 606/270 |
| 2011/0004248 A1 | 1/2011 | Abdou |
| 2011/0009906 A1 | 1/2011 | Hestad et al. |
| 2011/0137345 A1 | 6/2011 | Stoll et al. |
| 2011/0172708 A1 | 7/2011 | Fielding et al. |
| 2011/0245875 A1 | 10/2011 | Karim |
| 2011/0270314 A1 | 11/2011 | Mueller et al. |
| 2011/0288589 A1 | 11/2011 | Fielding et al. |
| 2012/0041441 A1 | 2/2012 | Bernstein et al. |
| 2012/0078303 A1 | 3/2012 | Malek |
| 2012/0109200 A1 | 5/2012 | Cahill et al. |
| 2012/0109202 A1 | 5/2012 | Kretzer et al. |
| 2012/0109210 A1 | 5/2012 | Baker et al. |
| 2012/0150231 A1* | 6/2012 | Alamin ............ A61B 17/7059 606/263 |
| 2013/0012955 A1 | 1/2013 | Lin |
| 2013/0035727 A1 | 2/2013 | Datta |
| 2013/0072983 A1 | 3/2013 | Lindquist et al. |
| 2013/0090692 A1 | 4/2013 | Nuckley et al. |
| 2013/0123854 A1 | 5/2013 | Kondrashov et al. |
| 2013/0150887 A1 | 6/2013 | McLean et al. |
| 2013/0238033 A1 | 9/2013 | Black |
| 2013/0325065 A1 | 12/2013 | Malandain et al. |
| 2013/0325068 A1 | 12/2013 | Fielding et al. |
| 2013/0345753 A1 | 12/2013 | Kretzer et al. |
| 2014/0025116 A1 | 1/2014 | Wei |
| 2014/0052183 A1 | 2/2014 | Freese |
| 2014/0074166 A1 | 3/2014 | Scarrow et al. |
| 2014/0094851 A1 | 4/2014 | Gordon |
| 2014/0135839 A1 | 5/2014 | Frankel et al. |
| 2014/0155940 A1 | 6/2014 | Dubois et al. |
| 2014/0222076 A1 | 8/2014 | Jackson |
| 2014/0257396 A1* | 9/2014 | Powers ............ A61B 17/7022 606/259 |
| 2014/0277142 A1 | 9/2014 | Blain et al. |
| 2014/0277145 A1 | 9/2014 | Reitblat et al. |
| 2014/0277163 A1 | 9/2014 | Kretzer et al. |
| 2014/0296917 A1 | 10/2014 | Donner et al. |
| 2015/0182263 A1 | 7/2015 | Donner et al. |
| 2015/0190178 A1 | 7/2015 | McCarthy et al. |
| 2016/0106478 A1 | 4/2016 | Simpson et al. |
| 2016/0143670 A1 | 5/2016 | Alamin et al. |
| 2016/0235447 A1* | 8/2016 | Mundis, Jr. ....... A61B 17/7031 |
| 2016/0242819 A1 | 8/2016 | Simpson et al. |

(56) References Cited

U.S. PATENT DOCUMENTS

| | | |
|---|---|---|
| 2016/0249957 A1 | 9/2016 | Deneuvillers |
| 2016/0287299 A1 | 10/2016 | Lang |
| 2016/0310170 A1 | 10/2016 | Carls |
| 2016/0354118 A1 | 12/2016 | Belliard et al. |
| 2017/0007299 A1 | 1/2017 | Mundis, Jr. et al. |
| 2017/0086889 A1 | 3/2017 | Padilla et al. |
| 2017/0231661 A1 | 8/2017 | Bannigan et al. |
| 2017/0281232 A1 | 10/2017 | Smith et al. |
| 2017/0281237 A1* | 10/2017 | Murray ............. A61B 17/7007 |
| 2017/0281246 A1 | 10/2017 | Murray et al. |
| 2017/0281247 A1 | 10/2017 | Murray et al. |
| 2017/0325850 A1 | 11/2017 | Acosta |
| 2017/0333087 A1 | 11/2017 | Lee et al. |
| 2017/0333088 A1 | 11/2017 | Lee et al. |
| 2017/0348024 A1 | 12/2017 | Abell et al. |
| 2017/0348026 A1 | 12/2017 | Stein et al. |
| 2018/0078286 A1 | 3/2018 | Le Couedic et al. |
| 2018/0110544 A1 | 4/2018 | Simpson et al. |
| 2018/0161069 A1 | 6/2018 | DiPaola |
| 2018/0168694 A1 | 6/2018 | Lee et al. |
| 2018/0228516 A1 | 8/2018 | Armstrong et al. |
| 2018/0228518 A1 | 8/2018 | Carruth et al. |
| 2018/0243009 A1 | 8/2018 | Bobbitt et al. |
| 2018/0243012 A1 | 8/2018 | Bobbitt et al. |
| 2018/0280062 A1 | 10/2018 | Lee et al. |
| 2018/0280063 A1 | 10/2018 | Lee et al. |
| 2018/0289403 A1 | 10/2018 | Shoshtaev |
| 2018/0353216 A1 | 12/2018 | Mundis, Jr. et al. |
| 2019/0029733 A1 | 1/2019 | Mickiewicz et al. |
| 2019/0029734 A1 | 1/2019 | Mickiewicz et al. |
| 2020/0015860 A1 | 1/2020 | Mickiewicz et al. |

FOREIGN PATENT DOCUMENTS

| | | |
|---|---|---|
| WO | 1999/044526 A1 | 9/1999 |
| WO | 2007/052975 A1 | 5/2007 |
| WO | 2009/099477 A2 | 8/2009 |

OTHER PUBLICATIONS

U.S. Appl. No. 15/663,865, filed Jul. 31, 2017, Connectors for Use in Systems and Methods for Reducing the Risk of Proximal Junctional Kyphosis.

U.S. Appl. No. 16/584,597, filed Sep. 26 2019, Connectors for Use in Systems and Methods for Reducing the Risk of Proximal Junctional Kyphosis.

[NoAuthorListed; YouTube™ webpage; "NILE™ Alternative Fixation Spinal System Product Animation," K2MInc, Mar. 25, 2015; retrieved online Dec. 7, 2017; <https://www.youtube.com/watch?v=7R76zxh5NkM >.

International Search Report and Written Opinion for Application No. PCT/US2018/044623, dated Dec. 10, 2018 (12 pages).

International Search Report and Written Opinion for Application No. PCT/US2018/044631, dated Dec. 12, 2018 (15 pages).

Extended European Search Report for Application No. 18841050.0, dated Mar. 30, 2021 (11 pages).

Extended European Search Report for Application No. 18842199.4, dated Apr. 6, 2021 (11 pages).

\* cited by examiner

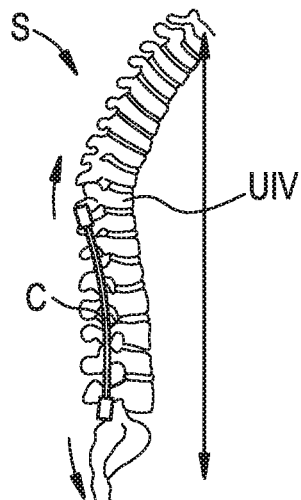
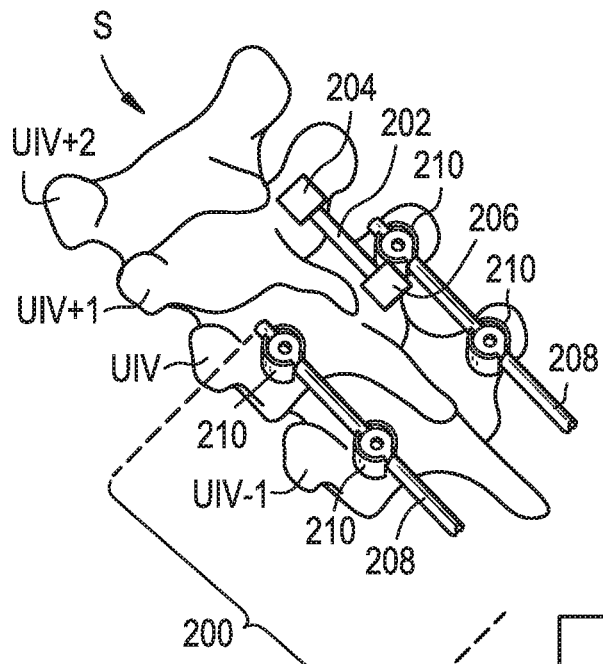
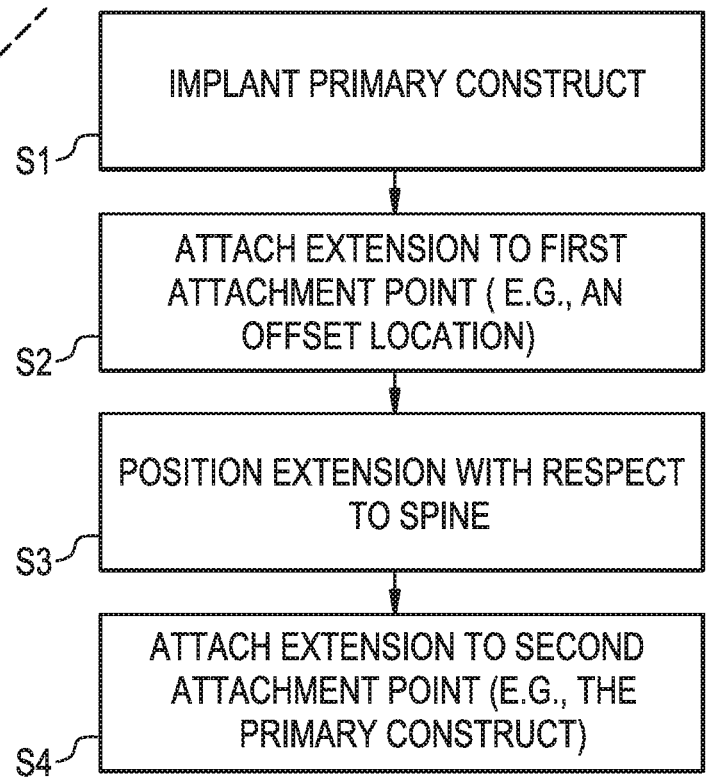

SYSTEMS AND METHODS FOR REDUCING THE RISK OF PROXIMAL JUNCTIONAL KYPHOSIS USING A BONE ANCHOR OR OTHER ATTACHMENT POINT

CROSS-REFERENCE TO RELATED APPLICATIONS

This application is a continuation of U.S. application Ser. No. 15/663,856, filed Jul. 31, 2017, which is hereby incorporated by reference in its entirety.

FIELD

Systems and methods for reducing the risk of proximal junctional kyphosis (PJK), proximal junctional failure (PJF), and other conditions are disclosed herein.

BACKGROUND

There are a number of spinal surgeries in which a fixation or stabilization construct is implanted in a patient and attached to the patient's spine. For example, a typical posterior fixation construct may include one or more longitudinal spinal rods attached to multiple of the patient's vertebrae by respective bone anchors. Exemplary bone anchors can include pedicle or lateral mass screws, hooks, wires, and so forth. The implanted construct extends along a segment of the spine between an uppermost instrumented vertebra (UIV), i.e., the most-superior or most-cranial vertebra to which the construct is attached, and a lowermost instrumented vertebra (LIV), i.e., the most-inferior or most-caudal vertebra to which the construct is attached.

One complication that can arise with these surgeries is an undesired degree of kyphosis at or above the UIV. Proximal junctional kyphosis (PJK) is typically defined as a proximal junctional sagittal Cobb angle greater than 10 degrees, or at least 10 degrees greater than in a pre-operative measurement. It is estimated that between 5% and 46% of adult spine patients suffer from some form of PJK, with most cases being diagnosed weeks or months after the surgery. In some cases, proximal junctional failure (PJF) can occur. PJF may be characterized by (i) post-operative fracture of the UIV or the vertebra superiorly-adjacent thereto (UIV+1), (ii) UIV implant failure, (iii) PJK increase greater than 15 degrees, and/or (iv) a need for proximal extension of the fusion or the construct within 6 months of the surgery. FIG. 1 is a sagittal view of a patient spine S in which PJK/PJF has occurred above the UIV after surgery to implant a fixation construct C. Patients who suffer from PJK or PJF may experience increased pain, neurologic deficit, or ambulatory difficulties, and may be faced with revision surgery and the expenses and risks associated therewith.

SUMMARY

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a bone anchor implanted in a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct, thereby providing a more-gradual transition from the instrumented vertebrae to the natural patient anatomy adjacent thereto. The extension can be placed with little or no soft tissue disruption.

In some embodiments, a surgical method can include attaching a primary construct to a spine of a patient, the primary construct extending between an uppermost instrumented vertebra (UIV) and a lowermost instrumented vertebra (LIV); attaching a flexible longitudinal extension to a first attachment point, the first attachment point being disposed superior to the UIV of the primary construct; positioning the extension relative to the patient's spine; and attaching the extension to a second attachment point, the second attachment point being disposed at or inferior to the UIV of the primary construct.

The first attachment point can include a bone anchor implanted in a vertebra disposed superior to the UIV of the primary construct. The first attachment point can be at least two vertebral levels superior to the UIV of the primary construct. The second attachment point can include a rigid spinal rod of the primary construct. The extension can have a stiffness that is greater than a stiffness of patient anatomy superior to the UIV of the primary construct and that is less than a stiffness of the primary construct. The extension can have a degree of spinal motion restriction that is greater than that of patient anatomy superior to the UIV of the primary construct and less than that of the primary construct. The extension can limit flexion of the spine without completely preventing such flexion. In some embodiments, vertebrae instrumented with the primary construct are fused to one another or prepared for such fusion and vertebrae to which the primary construct is extended by the extension are not fused or prepared for fusion. The primary construct can include a rigid spinal rod attached to first and second vertebrae by respective bone anchors. The method can include forming a primary incision through which the primary construct is implanted. The primary incision can terminate at a location inferior to a vertebra (UIV+1) that is superior-adjacent to the UIV of the primary construct. The extension can include a polymeric tether. The extension can exert extension forces on the patient's spine. The first attachment point can be a rib. The first attachment point can be a soft tissue structure of the patient. The extension can be attached to the first attachment point by a hook or a clamp. The extension can be attached to the first attachment point by a bone anchor through which the extension is threaded. Attaching the extension to the first attachment point can include driving a bone anchor into bone with the extension extending from the bone anchor and through a shaft of a driver instrument.

Positioning the extension can include passing the extension through a secondary incision disposed superior to a primary incision through which the primary construct is implanted. Positioning the extension can include passing the extension through the secondary incision and then pushing and/or pulling the extension in an inferior direction towards the primary construct, passing the extension beneath the skin and/or soft tissue disposed intermediate to the secondary incision and the primary construct. Positioning the extension can include passing an inserter instrument through the primary incision in a superior direction towards the secondary incision, contacting the extension with the inserter instrument, and pulling the extension in an inferior direction using the inserter instrument. Positioning the extension can include passing an inserter instrument through the secondary incision, coupling the extension to the inserter instrument, and pushing the inserter instrument and the extension coupled thereto in an inferior direction towards the primary construct, beneath the skin and/or soft-tissue disposed intermediate to the secondary incision and the primary construct. Positioning the extension can include inserting the extension through a primary incision through which the primary construct is implanted, and passing the extension in a superior direction towards the first attachment point while guiding the extension beneath the skin and/or soft tissue disposed intermediate to the first attachment point and the primary incision.

The extension can be attached to the second attachment point by a connector. The connector can clamp the extension to a spinal rod or a bone screw of the primary construct. The extension can be a first extension and the method can include placing a second extension on a contralateral side of the spinal midline from the first extension. Positioning the extension can include passing the extension superiorly from a primary incision through which the primary construct is implanted to the first attachment point, the extension passing beneath the skin and/or soft tissue of the patient, and attaching the extension to the first attachment point can include hooking a hook attached to the extension onto the first attachment point or clamping a clamp attached to the extension onto the first attachment point. In some embodiments, no portion of the extension is disposed anterior to any lamina of the patient's spine when the extension is attached to the first and second attachment points.

In some embodiments, a surgical method can include forming a primary incision in a patient; attaching a primary construct to the patient's spine via the primary incision; forming a secondary incision in the patient at a location superior to the primary incision; inserting a bone anchor through the secondary incision with an elongate flexible tether attached to the bone anchor; driving the bone anchor into bone at a first attachment point, thereby attaching the tether to the first attachment point while a portion of the tether extends through the second incision to a location outside the patient; tunneling the tether beneath soft tissue disposed intermediate to the primary incision and the secondary incision; and attaching the tether to the primary construct via the primary incision.

Tunneling the tether can include inserting an inserter instrument through the secondary incision and pushing the instrument inferiorly towards the primary incision. The method can include grasping a leading end of the inserter instrument via the primary incision and pulling the inserter instrument through the primary incision. The tether can be attached to the inserter instrument and can be carried along the same path as the inserter instrument, thereby positioning the tether such that it extends along the patient's spine between the first attachment point and the primary construct.

In some embodiments, a surgical system can include a primary construct comprising a rigid spinal fixation rod and first and second bone anchors configured to attach the spinal rod to first and second vertebrae; an elongate flexible tether attached to a tether anchor; a driver instrument for driving the tether anchor into bone while the tether extends from the tether anchor; and a connector configured to clamp the tether to the spinal rod of the primary construct.

BRIEF DESCRIPTION OF THE DRAWINGS

FIG. 1 is a sagittal view of the spine of a human patient suffering from PJK/PJF;

FIG. 2A is a perspective view of a human spine with a primary construct and a longitudinal extension attached thereto;

FIG. 2B is a flow chart of a surgical method;

DETAILED DESCRIPTION

Figure 3A:
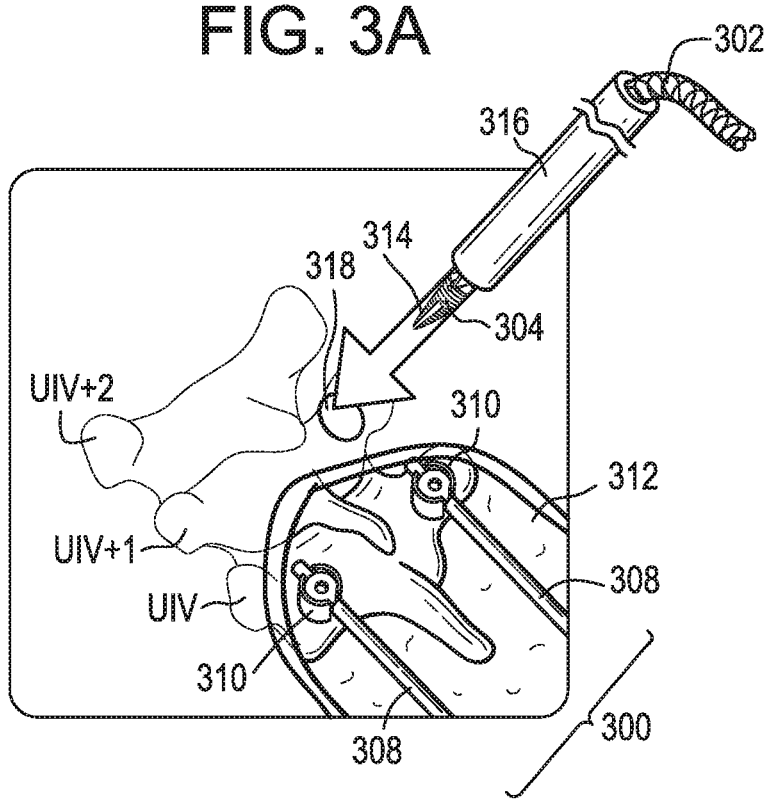
FIG. 3A is a perspective view of a human spine with a bone anchor being attached thereto.

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a bone anchor implanted in a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct, thereby providing a more-gradual transition from the instrumented vertebrae to the natural patient anatomy adjacent thereto. The extension can be placed with little or no soft tissue disruption.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

FIGS. 2A-2B schematically illustrate a system and method for treating, preventing, or reducing the risk of proximal junctional kyphosis, proximal junctional failure, and other conditions. As shown, a primary construct 200 can be implanted in a patient and attached to the patient's spine S. The primary construct 200 can be extended to one or more additional vertebral levels by (i) attaching a longitudinal extension 202 to a first attachment point 204, (ii) positioning the longitudinal extension relative to the patient's spine, and (iii) attaching the longitudinal extension to a second attachment point 206. The first attachment point 204 can be an implant or an anatomical structure that is longitudinally offset from the primary construct 200, e.g., one or more vertebral levels superior to the UIV of the primary construct. The extension 202 can be attached to the first attachment point 204 in a manner that does not disrupt or only minimally disrupts soft tissue in the vicinity of the first attachment point. The second attachment point 206 can be an implant or an anatomical structure disposed at or below the UIV of the primary construct 200. For example, the second attachment point can be a rod 208, bone anchor 210, or other component of the primary construct 200 itself, or a vertebra to which the primary construct is attached. The above steps can be performed in any sequence. For example, the extension 202 can be implanted prior to the primary construct 200. As another example, the extension 202 can be attached to the first attachment point 204 after placing the extension in its final position relative to the spine and/or after attaching the extension to the second attachment point 206.

The extension can provide a step-down in stiffness and/or spinal motion restriction between the primary construct (which is typically relatively rigid and immobile) and the natural soft tissue and other patient anatomy superior to the primary construct (to which there is generally no implant-based rigidity or mobility restriction applied). The extension can have a stiffness that is greater than the natural patient anatomy and less than the primary construct. The extension can have a degree of spinal motion restriction that is greater than the natural patient anatomy and less than the primary construct. The extension can help insulate the patient anatomy superior to the primary construct from forces and stress that may contribute to PJK/PJF. The extension can provide a soft link between the primary construct and undisturbed soft tissue superior thereto. The extension can constrain or limit flexion of the spine to reduce the risk of PJK/PJF. The extension can replicate the natural soft tissue envelope. In some embodiments, the vertebrae instrumented with the primary construct are fused to one another and the vertebrae to which the primary construct is extended by the extension are not fused. Accordingly, a hybrid construct can be formed in which a first spinal segment is instrumented and fused, a second spinal segment superior to the first segment is instrumented and not fused, and a third spinal segment superior to the second segment is neither instrumented nor fused.

Referring now to FIG. 2B, in a step S1, a primary construct can be implanted in the patient. The primary construct can include one or more spinal rods extending longitudinally along the patient's spine. The spinal rod or rods can be attached to the patient's spine using bone anchors such as pedicle or lateral mass screws, hooks, wires, and so forth. The primary construct can extend along a segment of the spine between an uppermost instrumented vertebra (UIV) of the primary construct, i.e., the most-superior or most-cranial vertebra to which the primary construct is attached, and a lowermost instrumented vertebra (LIV) of the primary construct, i.e., the most-inferior or most-caudal vertebra to which the primary construct is attached. The UIV can be the uppermost vertebra in which a bone screw of the primary construct is implanted. The LIV can be the lowermost vertebra in which a bone screw of the primary construct is implanted. The primary construct can be implanted using any of a variety of known techniques, including open procedures, minimally-invasive or percutaneous procedures, and so forth. The primary construct can be implanted through a primary incision. The primary incision can extend longitudinally along the patient's spine. The terminal superior end of the primary incision can be located inferior to UIV+1, inferior to UIV, and/or inferior to UIV-1. The primary incision can include a plurality of discrete incisions, e.g., in the case of minimally-invasive procedures for installing the primary construct. The primary construct can include a rigid spinal rod, e.g., a rod that does not materially bend or deform post-implantation when subjected to normal anatomical loads, or a rod which is not designed to bend or deform under such conditions.

In a step S2, a longitudinal extension can be attached to a first attachment point, e.g., a location within the patient that is offset from the primary construct. The extension can be or can include any of a variety of elements for extending the primary construct to one or more additional vertebral levels. For example, the extension can be a tether, cable, cord, mesh, fabric, tape, film, or wire. The extension can be flexible. The extension can have a stiffness that is less than that of the primary construct or a component thereof, e.g., less than a stiffness of a spinal rod of the primary construct. The extension can have a stiffness that is greater than that of the natural spinal anatomy, e.g., greater than that of the ligaments and other soft tissue that connect the vertebrae.

The extension can be a length of MERSILENE tape available from ETHICON of Somerville, N.J. The extension can be a length of non-absorbable, braided, sterile material. The extension can be formed from poly (ethylene terephthalate). The extension can be formed from fibers of high molecular weight, long-chain, linear polyesters having recurrent aromatic rings. The extension can be coated with anti-bacterial agents, corticosteroids, anti-infective agents, tryclosan, and so forth. The extension can be radiopaque, radiolucent, or partially radiopaque and partially radiolucent. The extension can include imaging bands or markers. The extension can be polymeric. The extension can be formed from or can include various materials including polyethylene terephthalate or DACRON, polytetrafluoroethylene or TEFLON, poly-paraphenylene terephthalamide or KEVLAR, ultra-high-molecular-weight polyethylene (UHMWPE), nylon, poly(L-lactic acid), and the like. The extension can be reinforced with materials including metals, elastomers, carbon fibers, etc. The extension can include resilient or shape memory materials such as elastomers or nitinol. Such materials can allow the extension to not only limit flexion of the spine, but also to instill extension forces, which may improve lordosis and/or reinforce posterior soft tissues. The extension forces can be tailored based upon material properties, weaving structure, thickness, or other attributes of the extension.

The extension can be a tether that is substantially flat or planar. The tether can have a cross-sectional width that is greater than a cross-sectional height. For example, the width can be at least two times greater than the height. The width of the tether can be in the range of about 4 mm to about 8 mm. The height of the tether can be in the range of about 0.5 mm to about 2.5 mm. The tether can have any number of different cross-sections, including rectangular, square, elliptical, circular, and so forth.

The extension can be attached to a first attachment point that is offset from the primary construct, e.g., one or more vertebral levels superior to the primary construct. The first attachment point can be a vertebra. The first attachment point can be a pedicle, a transverse process, a lamina, a facet, a spinous process, or a vertebral body of the vertebra. The first attachment point can be an implant implanted in any of the above locations. The vertebra can be superior to UIV. The vertebra can be UIV+1, UIV+2, or higher. The first attachment point can be a rib or other anatomical anchor point. The first attachment point can be a bone structure. The first attachment point can be a soft tissue structure. The first attachment point can be a muscle, a tendon, or a ligament. The extension can be attached to a plurality of the above-described first attachment points.

The extension can be attached to the first attachment point in any of a variety of ways. The extension can be attached to the first attachment point using a suture, rivet, or staple. The extension can be attached to the first attachment point using a clamp. The clamp can be attached to a lamina, spinous process, or other anatomical structure or implant. The extension can be attached to the first attachment point using a hook. The hook can be hooked onto a lamina, spinous process, or other anatomical structure or implant. The extension can be attached to the first attachment point using a bone anchor, e.g., a screw anchor, a suture anchor, an expandable anchor, a tether anchor, and/or a soft-tissue anchor, any of which may be of the type available from DEPUY SYNTHES of Raynham, Mass.

The extension can be attached to the first attachment point in a way that minimizes soft tissue disruption. The extension can be positioned at the first attachment point without extending the primary incision and/or without forming any incision other than the primary incision. The extension can be positioned at the first attachment point through a small secondary incision formed over the first attachment point. The secondary incision can be percutaneous stab incision. The secondary incision can be made only as large as necessary to pass the extension therethrough, or only as large as necessary to pass an anchor for attaching the extension therethrough. The secondary incision can have a length that is equal or substantially equal (e.g., within 10% of) a corresponding dimension of the extension. The secondary incision can have a diameter that is equal or substantially equal (e.g., within 10% of) a diameter of a bone anchor used to attach the extension to the first attachment point. The secondary incision can have a length or diameter that is less than about 10 mm, less than about 5 mm, less than about 3 mm, and/or less than about 1 mm. The extension, or at least one end thereof, the anchor, or both the extension and the anchor, can be delivered to the first attachment point through a trocar, tube, or cannula. The extension can be attached to the first attachment point without disturbing the soft tissue envelope of the vertebral levels superior to the primary construct.

In a step S3, the extension can be positioned relative to the patient's spine. The extension can be positioned to extend along the patient's spine between the first attachment point and a second attachment point, such as the primary construct.

The extension can be passed through the secondary incision and then pushed and/or pulled in an inferior direction towards the primary construct, passing the extension beneath the skin and/or soft tissue disposed intermediate to the secondary incision and the primary construct. The extension can be pushed and/or pulled in the inferior direction by an inserter or tunneling instrument. The inserter instrument can be passed through the primary incision and up towards the secondary incision to grab the extension before pulling it inferiorly. The inserter instrument can be passed through the secondary incision and pushed with the extension coupled thereto inferiorly towards the primary construct, beneath the skin and/or soft-tissue.

The extension can be inserted through the primary incision and passed in a superior direction towards the first attachment point, guiding the extension beneath the skin and/or soft tissue disposed intermediate to the first attachment point and the primary incision. The extension can be passed in the superior direction using forceps, a pushrod, or other inserter instrument.

The extension can be positioned along a posterior aspect of the spine. The extension can be positioned along an anterior or lateral aspect of the spine. The extension can be positioned such that no portion of the extension is disposed anterior to any lamina of the patient's spine.

The extension can be positioned in a way that minimizes soft tissue disruption. The extension can be positioned without extending the primary incision and/or without forming any incision other than the primary incision. The extension can be positioned without disturbing the soft tissue envelope of the vertebral levels superior to the primary construct.

In a step S4, the extension can be attached to a second attachment point. The second attachment point can be inferior to the first attachment point. The second attachment point can be a spinal rod, a bone anchor or bone screw, a cross-connector, or any other component of the primary construct. The second attachment point can be an anatomical structure adjacent or inferior to the primary construct.

The second attachment point can be a vertebra. The second attachment point can be a pedicle, a transverse process, a lamina, a facet, a spinous process, or a vertebral body of the vertebra. The second attachment point can be an implant implanted in any of the above locations. The vertebra can be inferior to the UIV of the primary construct. The vertebra can be UIV, UIV-1, UIV-2, or lower. The second attachment point can be a rib or other anatomical anchor point. The second attachment point can be a bone structure. The second attachment point can be a soft tissue structure. The second attachment point can be a muscle, a tendon, or a ligament. The extension can be attached to a plurality of the above-described second attachment points.

The extension can be attached to the second attachment point in any of a variety of ways. The extension can be attached to the second attachment point using a suture, rivet, or staple. The extension can be attached to the second attachment point using a clamp. The clamp can be attached to a lamina, spinous process, or other anatomical structure or implant. The extension can be attached to the second attachment point using a hook. The hook can be hooked onto a lamina, spinous process, or other anatomical structure or implant. The extension can be attached to the second attachment point using a bone anchor, e.g., a screw anchor, a suture anchor, an expandable anchor, a tether anchor, and/or a soft-tissue anchor, any of which may be of the type available from DEPUY SYNTHES of Raynham, Mass.

The second attachment point can be a spinal rod. The extension can be attached to the spinal rod using a clamp or connector that receives the rod and the extension.

The second attachment point can be a bone anchor, e.g., a screw or a hook. The extension can be attached to the bone anchor using a clamp or connector that receives the bone anchor and the extension. The extension can be clamped between a spinal rod and a rod seat of the bone anchor. The extension can be clamped between a spinal rod and a set screw or closure mechanism of the bone anchor. The bone anchor can include a first set screw or closure mechanism for locking the extension to the bone anchor and a second set screw or closure mechanism for locking a spinal rod to the bone anchor.

The above steps can be repeated to attach multiple extensions to the patient's spine. The multiple extensions can share common attachment points or can be attached at different locations. For example, first and second extensions can be placed in parallel on contralateral sides of the spinal midline. Inferior ends of the extensions can be attached to respective spinal rods and/or respective bone anchors of a primary construct. Superior ends of the extensions can be attached to respective attachment points longitudinally offset from the primary construct, or to a common attachment point such as a spinous process of a superior vertebra.

FIGS. 3A-3E illustrate an example of the systems and methods described above. In FIG. 3A, a primary construct 300 is implanted in a patient using known techniques. The primary construct 300 can be implanted though a primary incision 312. The primary construct 300 can include first and second spinal rods 308 coupled to the patient's vertebrae by respective bone anchors 310. Only the UIV of the primary construct 300 is shown, though it will be appreciated that the primary construct can extend inferiorly to one or more additional vertebrae. As also shown in FIG. 3A, a screw-type bone anchor 314 with a flexible tether 302 attached thereto can be driven into a vertebra superior to the primary construct 300, e.g., UIV+1 as shown. The tether 302 can serve as a longitudinal extension and the anchor 314 can define the first attachment point 304. The anchor 314 can be delivered and/or driven into the bone with a driver instrument 316. The driver instrument 316 can define a central passage in which the tether 302 can be stored during anchor insertion. The anchor 314 can be delivered through a small secondary incision 318 disposed superior to the primary incision 312 with little or no disruption to the soft tissue envelope. The anchor 314 can include a threaded bone-engaging portion. The anchor 314 can include an inner lumen in which at least a portion of the tether 302 is disposed.

Figure 3B:
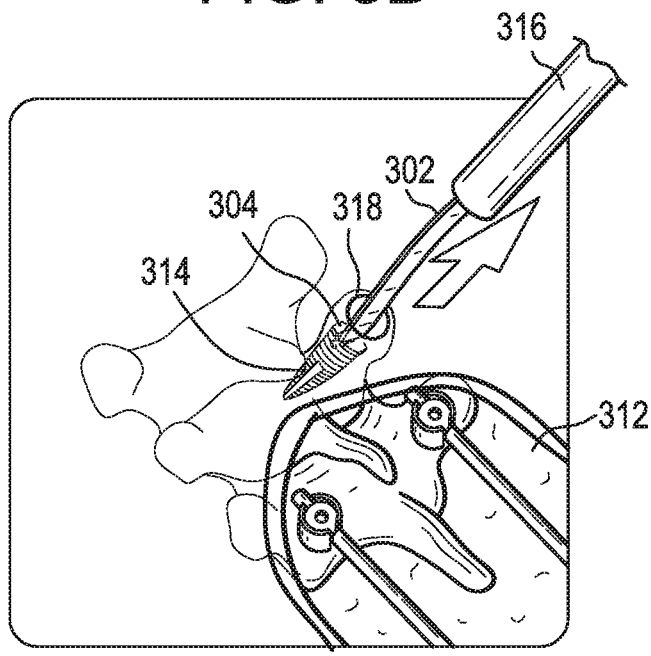
FIG. 3B is a perspective view of a driver instrument being removed from the bone anchor of FIG. 3A.

As shown in FIG. 3B, after driving the anchor 314 into bone, the driver instrument 316 can be withdrawn proximally, leaving the tether 302 extending from the anchor 314, with the anchor 314 now serving as a first attachment point 304. The tether 302 can extend through the secondary incision 318 to a location external to the patient. The tether 302 can be fixed to the anchor 314 or can be threaded or looped through an aperture formed in the anchor or around a post disposed in a lumen of the anchor.

Figure 3C:
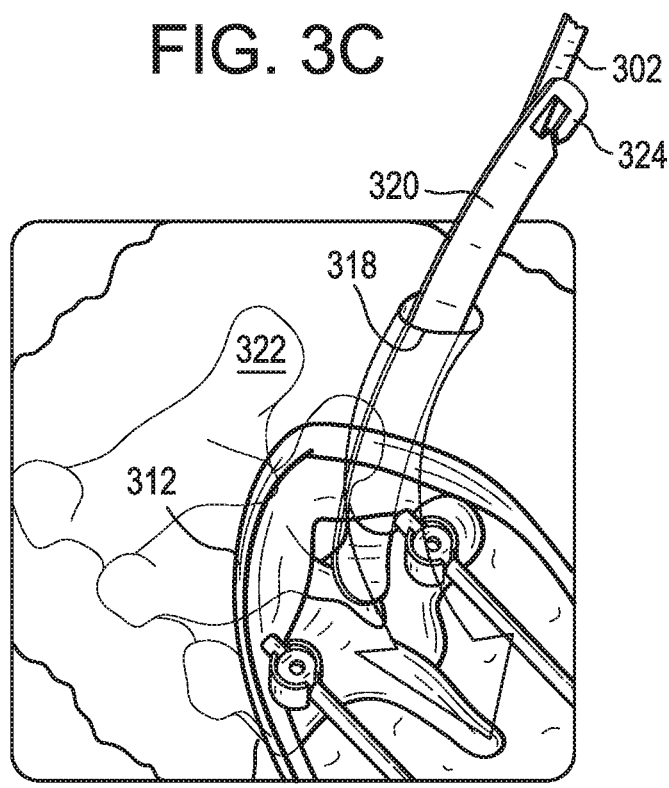
FIG. 3C is a perspective view of an inserter instrument inserted through a secondary incision.

As shown in FIG. 3C, an inserter or tunneling instrument 320 can be passed through the secondary incision 318 and pushed inferiorly towards the primary incision 312 through or beneath the patient's skin and/or soft tissue 322. The inserter instrument 320 can be rigid or semi-rigid to facilitate pushing of the instrument through the patient. The inserter instrument 320 can include a hook, aperture, or other attachment 324 for attaching the inserter instrument to the tether 302. The attachment 324 can be disposed at or near a proximal or trailing end of the inserter instrument 320. The leading end of the inserter instrument 320 can be pushed through the secondary incision 318 and towards the primary incision 312. A user can then reach into the primary incision 312, grasp the leading end of the inserter instrument 320, and pull the inserter instrument through the primary incision.

Figure 3D:
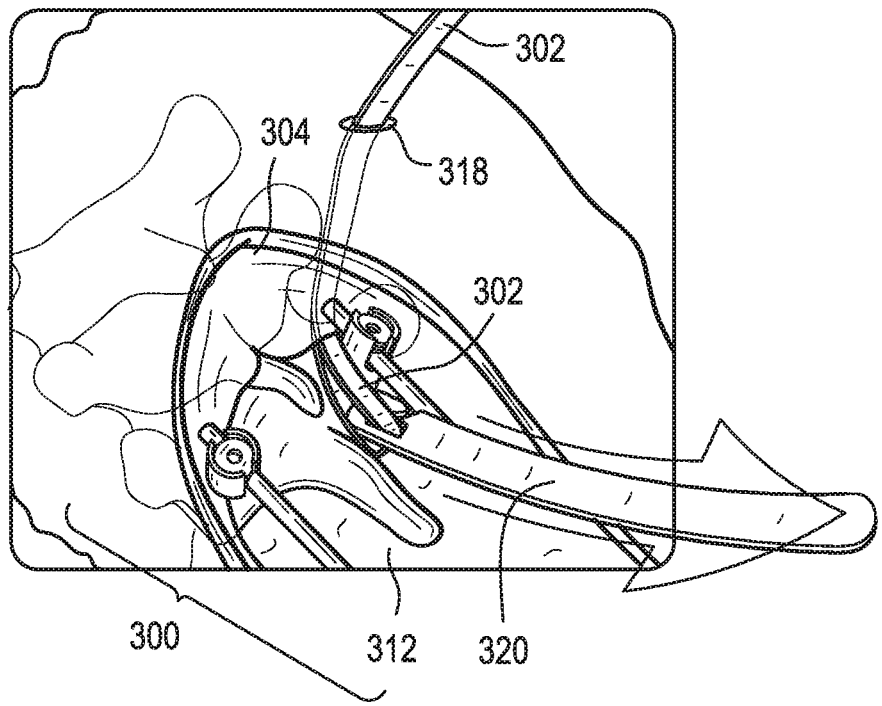
FIG. 3D is a perspective view of the inserter instrument pulling a tether through the patient.

As shown in FIG. 3D, the tether 302 can be pulled along the same path as the inserter instrument 320, thereby positioning the tether such that it extends along the patient's spine between the first attachment point 304 and the primary construct 300.

Figure 3E:
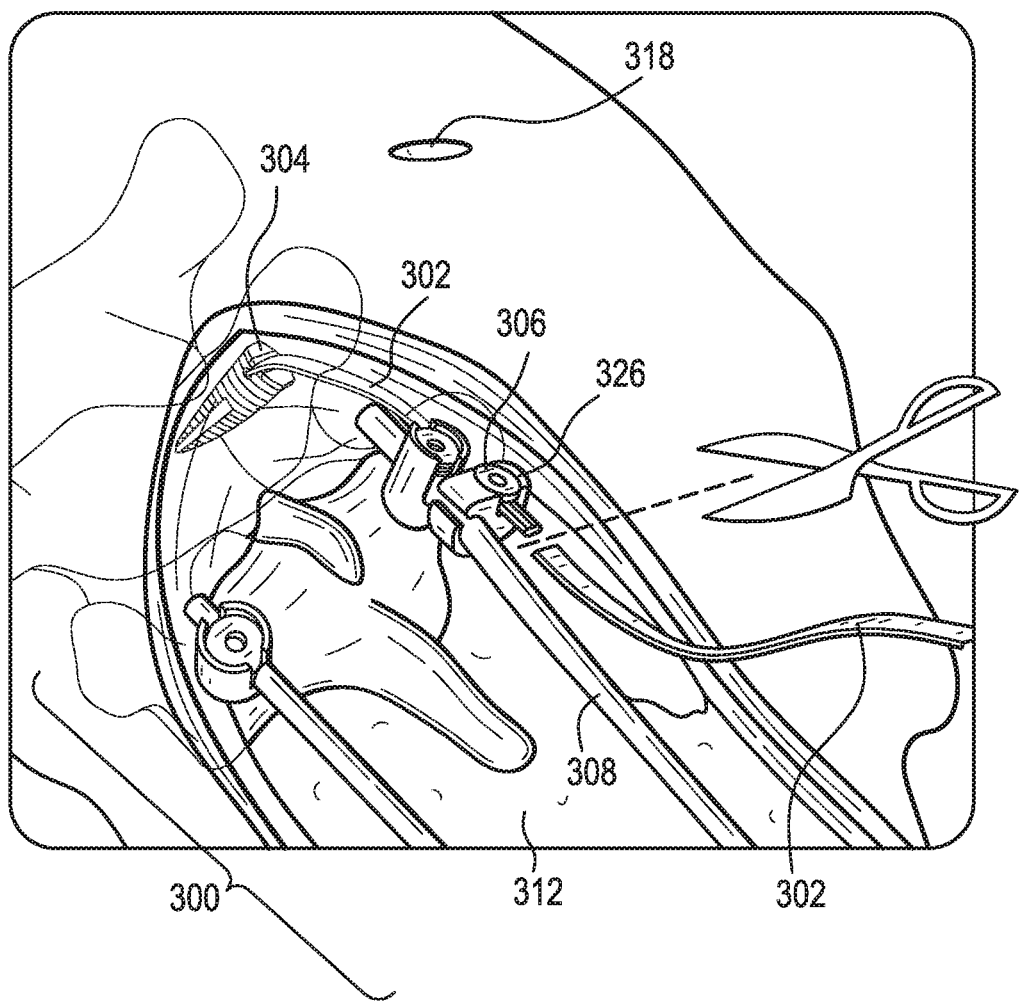
FIG. 3E is a perspective view of the tether being attached to a spinal rod by a connector.

As shown in FIG. 3E, the tether 302 can be attached to the primary construct 300 or to another second attachment point 306. For example, the tether 302 can be tied off to the primary construct 300 or, as shown, a tether-to-rod connector 326 can be used to attach the tether to a spinal rod 308 of the primary construct. Any excess length of the tether 302 can be cut off and discarded.

Figure 4:
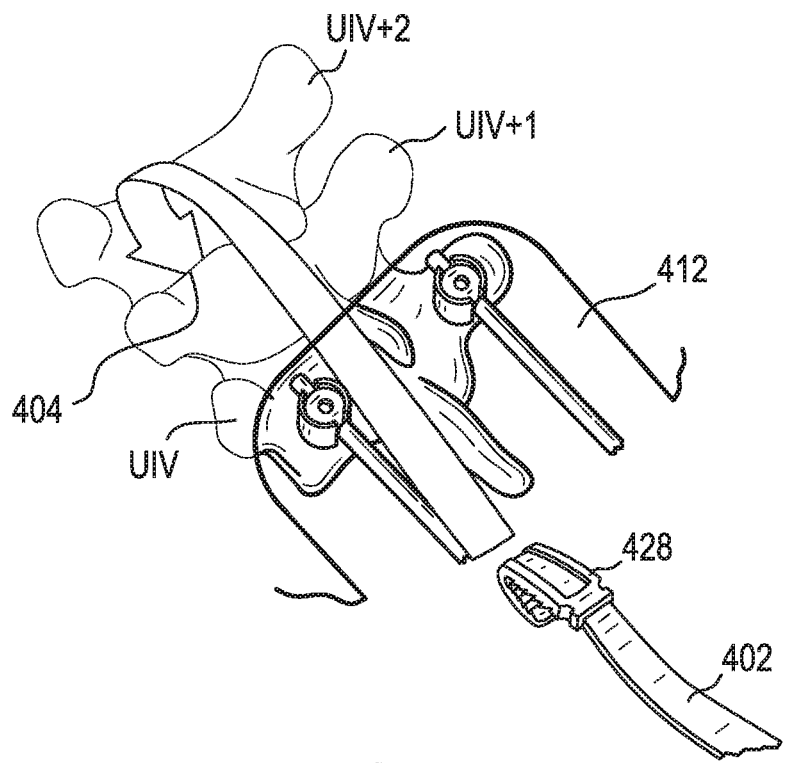
FIG. 4 is a perspective view of an extension with a hook being attached to a patient.
Figure 5:
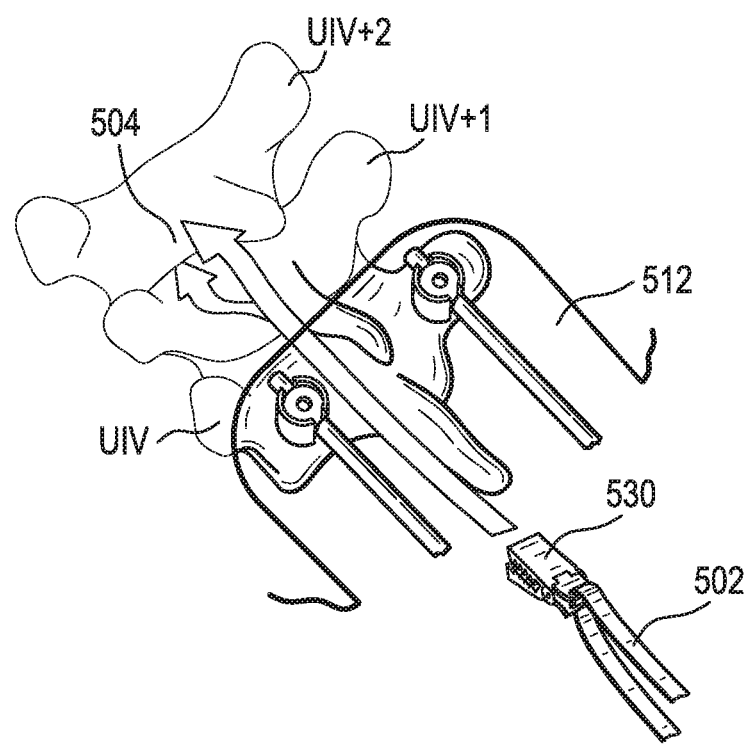
FIG. 5 is a perspective view of an extension with a clamp being attached to a patient.
Figure 6A:
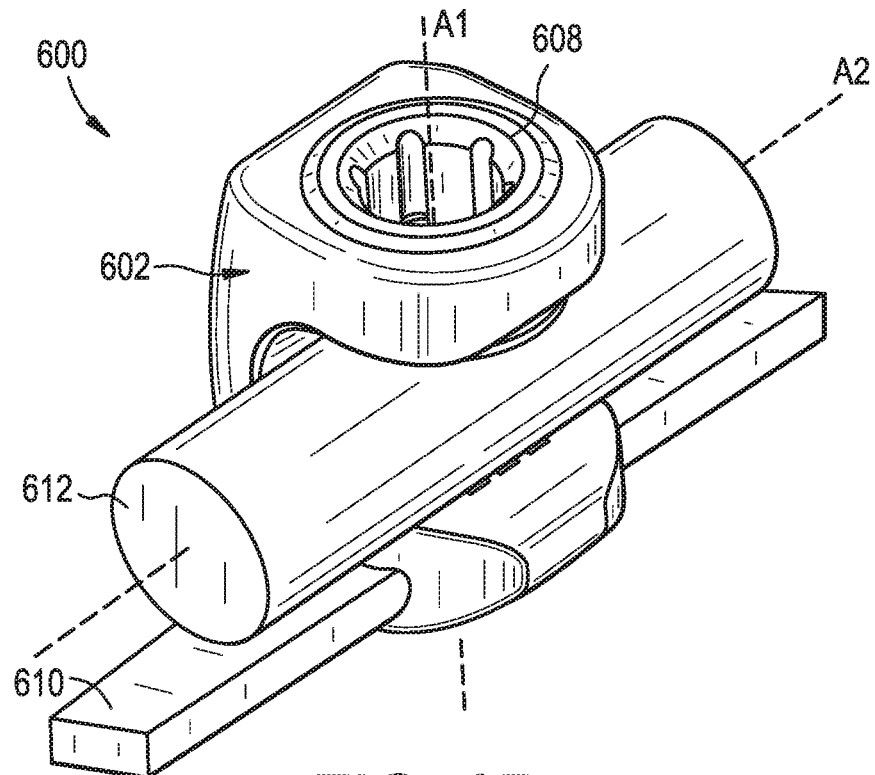
FIG. 6A is a perspective view of a connector that attaches a spinal rod to a tether.
Figure 6B:
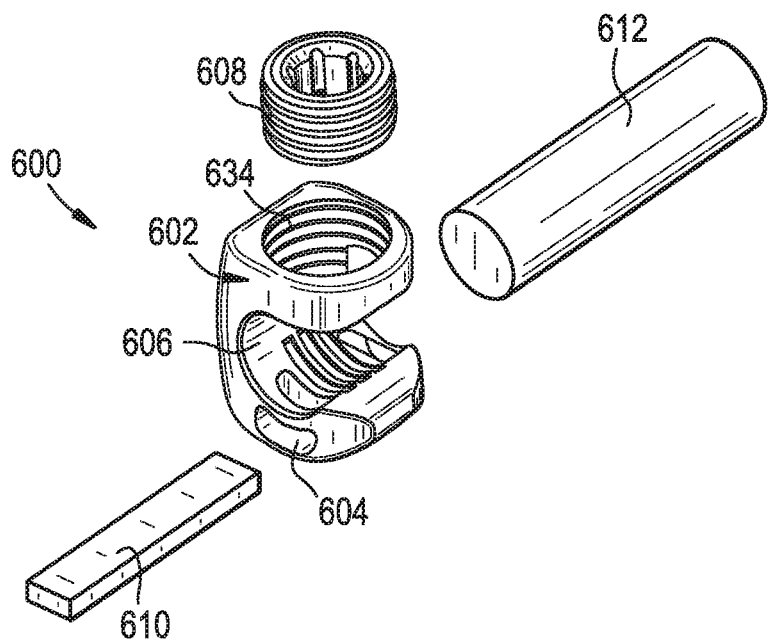
FIG. 6B is an exploded perspective view of the connector, tether, and rod of FIG. 6A.
Figure 6C:
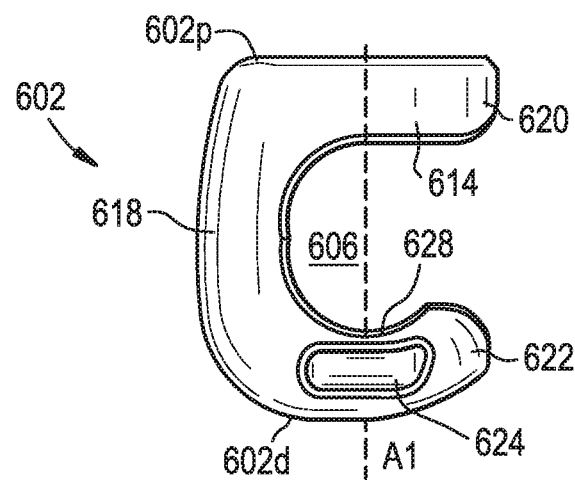
FIG. 6C is a front view of a body of the connector of FIG. 6A.
Figure 6D:
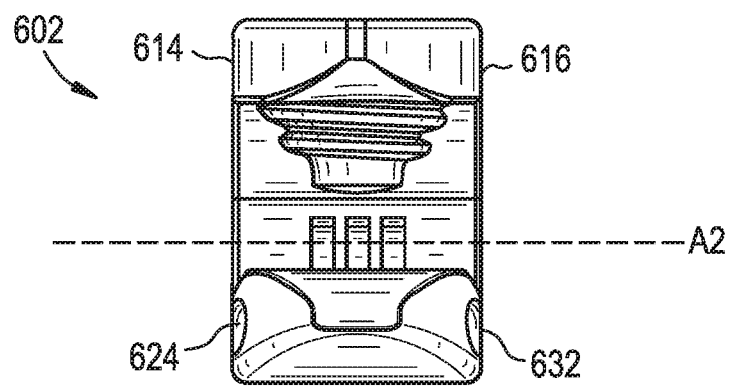
FIG. 6D is a side view of the body of FIG. 6C.
Figure 6E:
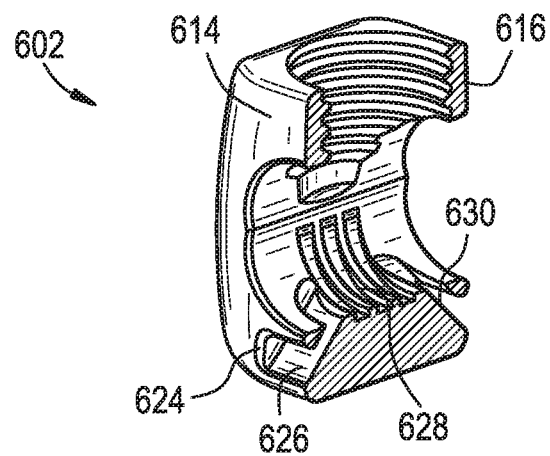
FIG. 6E is a sectional perspective view of the body of FIG. 6C.

It will be appreciated that the above method can be varied in numerous ways. For example, as shown in FIG. 4, an extension 402 with a hook 428 mounted thereto, e.g., at a terminal end thereof, can be passed superiorly from the primary incision 412 to the first attachment point 404, beneath the skin and/or soft tissue of the patient. The hook 428 can be hooked onto any of a variety of anatomical structures of the patient, such as a lamina of UIV+1 as shown or of a more-superior vertebra. In such a method, the need for a secondary incision and/or a bone anchor can be eliminated. By way of further example, as shown in FIG. 5, an extension 502 with a clamp 530 mounted thereto, e.g., at a terminal end thereof, can be passed superiorly from the primary incision 512 to the first attachment point 504, beneath the skin and/or soft tissue of the patient. The clamp 530 can be clamped onto any of a variety of anatomical structures of the patient, such as a lamina of UIV+2 as shown, of a more-superior vertebra, or of UIV+1. In such a method, the need for a secondary incision and/or a bone anchor can be eliminated. The clamp 530 can include opposed jaws that are biased towards one another, e.g., by a spring.

FIGS. 6A-6E illustrate an exemplary connector 600 that can be used in the above methods to attach the extension to the primary construct. For example, the connector 600 can be used to attach a spinal rod of the primary construct to an elongate flexible tether or other type of extension.

As shown, the connector 600 can include a body 602 that defines a tether slot or channel 604 and a rod slot or channel 606. The connector 600 can also include a locking element or set screw 608 that can be actuated to lock the connector 600 to a tether 610 and to a rod 612. The connector 600 can allow for simultaneous locking to the tether 610 and to the rod 612.

The body 602 can include proximal and distal ends 602p, 602d that define a central proximal-distal axis A1. The body 602 can include opposed end walls 614, 616, a vertical sidewall 618, and proximal and distal arms 620, 622 extending laterally from the vertical sidewall. The arms 620, 622 can define the rod slot 606 therebetween. At least a portion of the tether slot 604 can also be defined between the arms 620, 622. A rod 612 disposed in the rod slot 606 can have a central longitudinal rod axis A2. The rod slot 606 can be open in a lateral direction, such that a rod can be inserted into the rod slot by moving the rod laterally with respect to the connector 600 or vice versa. Each of the arms 620, 622 can extend from the vertical sidewall 618 to a free end. The body 602 can thus be C-shaped in a plane perpendicular to the rod axis A2.

The tether slot 604 can extend from an opening 624 formed in the end wall 614 of the distal arm 622, through a first tunnel 626 formed in the distal arm, across a proximal-facing clamping surface 628 of the distal arm, through a second tunnel 630 formed in the distal arm, and to an opening 632 formed in the opposite end wall 616 of the distal arm. The clamping surface 628 can include grooves, ridges, teeth, or other features for enhancing grip or friction between the connector 600 and a tether 610 disposed in the tether slot 604. The first and second tunnels 626, 630 can extend at an oblique angle with respect to the axis A1, the axis A2, and/or the clamping surface 628. The first and second tunnels 626, 630 can extend in a distal-to-proximal direction as they approach the axis A1. The first and second openings 624, 632 and/or the first and second tunnels 626, 630 can have a cross-section in a plane perpendicular to the axis A2 that substantially corresponds to that of the tether 610, e.g., a substantially rectangular cross-section.

The proximal arm 620 can include an opening 634 configured to receive the set screw 608. The opening 634 can include interior threads that engage with an exterior thread of the set screw 608. Accordingly, the set screw 608 can move along the axis A1 by rotating the set screw about the axis A1 relative to the body 602. While a set screw 608 is shown, it will be appreciated that other locking elements can be used instead or addition, such as a closure cap that advances and locks by quarter-turn rotation, a closure cap that slides in laterally without rotating, a threaded nut, and so forth.

In use, a tether 610 can be positioned within the tether slot 604 and a rod 612 can be positioned within the rod slot 606. The tether 610 can be pulled through the tether slot 604 until the desired tension is applied to the patient's spine. The set screw 608 can then be tightened to advance the set screw distally relative to the body 602 and to urge the rod 612 towards the clamping surface 628, thereby clamping the tether 610 between the rod and the clamping surface. When the set screw 608 is tightened, the rod 612 can be locked to the connector 602 such that the rod cannot rotate or translate relative to the connector. Similarly, when the set screw 608 is tightened, the tether 610 can be locked to the connector 600 such that the tether cannot rotate or translate relative to the connector.

Figure 7:
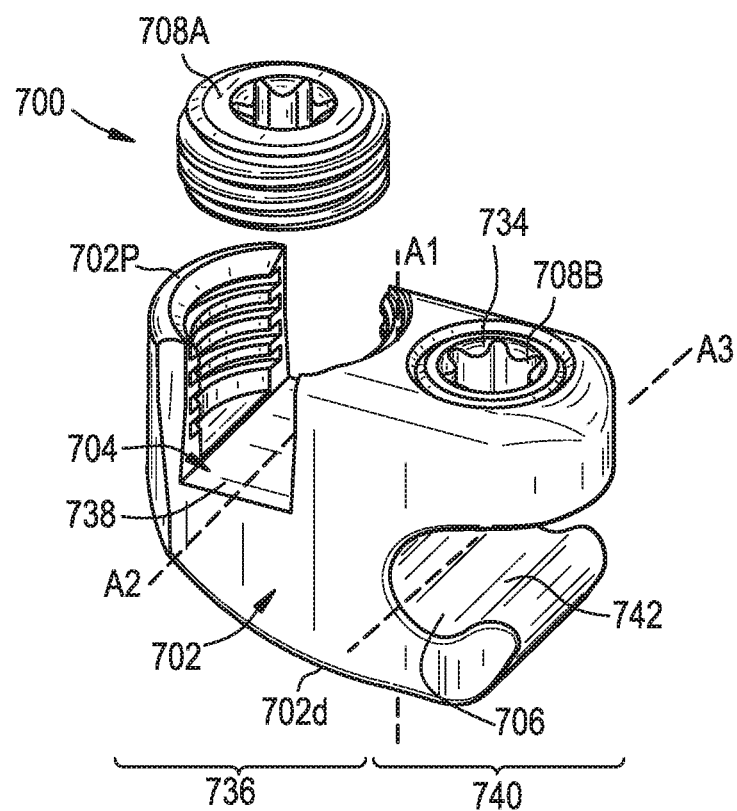
FIG. 7 is a perspective view of a connector for attaching a rod to a tether, the connector having a side-loading rod slot.

FIG. 7 illustrates another exemplary connector 700 that can be used in the above methods to attach the longitudinal extension to the primary construct. For example, the connector 700 can be used to attach a spinal rod of the primary construct to an elongate flexible tether or other type of extension.

As shown, the connector 700 can include a body 702 that defines a tether slot or channel 704 and a rod slot or channel 706. The connector 700 can also include a first locking element or set screw 708A that can be actuated to lock the connector 700 to a tether and a second locking element or set screw 708B that can be actuated to lock the connector to a rod. The connector 700 can allow for independent locking to the rod and to the tether.

The body 702 can include proximal and distal ends 702p, 702d that define a central proximal-distal axis A1.

The body 702 can include a first portion 736 with opposed arms that define the tether slot 704 therebetween. The arms can include interior threads or can be otherwise configured to mate with the first locking element 708A. A tether clamping surface 738 can be defined between the opposed arms. The clamping surface 738 can include grooves, ridges, teeth, or other features for enhancing grip or friction between the connector 700 and a tether disposed in the tether slot 704. The tether slot 704 can be open in a proximal direction, such that a tether can be inserted into the slot by moving the tether distally with respect to the connector 700. A tether disposed in the tether slot can extend along a tether axis A2. The axis A2 can be perpendicular to the axis A1.

The body 702 can include a second portion 740 with opposed arms that define the rod slot 706 therebetween. The proximal arm can include a threaded recess 734 or can be otherwise configured to mate with the second locking element 708B. A rod clamping surface 742 can be defined between the opposed arms. The rod slot 706 can be open in a lateral direction, such that a rod can be inserted into the slot by moving the rod laterally with respect to the connector 700. A rod disposed in the rod slot 706 can extend along a rod axis A3. The axis A3 can be perpendicular to the axis A1. The axis A3 can be parallel to the axis A2.

The body 702 can have a UC-shape in a plane perpendicular to the tether axis A2 and the rod axis A3.

While first and second set screws 708A, 708B are shown, it will be appreciated that other locking elements can be used instead or addition, such as a closure cap that advances and locks by quarter-turn rotation, a closure cap that slides in laterally without rotating, a threaded nut, and so forth.

In use, a tether can be positioned within the tether slot 704 and a rod can be positioned within the rod slot 706. The first and second set screws 708A, 708B can be tightened to lock the tether and the rod to one another and to the connector 700. The first and second set screws 708A, 708B can be tightened in any sequence, and can allow for independent locking of the rod and the tether to the connector 700. Prior to locking, the tether can be pulled through the tether slot 704 until the desired tension is applied to the patient's spine. The first set screw 708A can be tightened to advance the set screw distally relative to the body 702 and to clamp the tether against the tether clamping surface 738. When the first set screw 708A tightened, the tether can be locked to the connector 700 such that the tether cannot rotate or translate relative to the connector. The second set screw 708B can be tightened to advance the second set screw distally relative to the body 702 and to clamp the rod against the rod clamping surface 742. When the second set screw 708B is tightened, the rod can be locked to the connector 700 such that the rod cannot rotate or translate relative to the connector.

Figure 8:
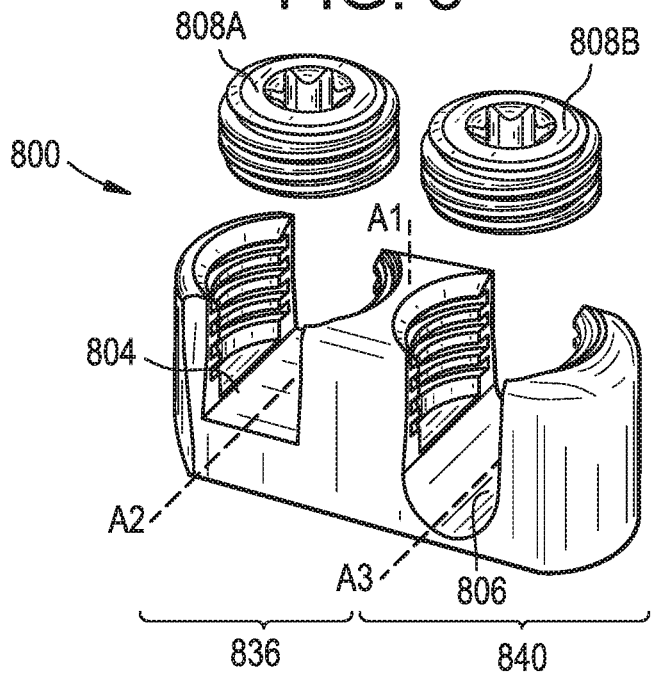
FIG. 8 is a perspective view of a connector for attaching a rod to a tether, the connector having a top-loading rod slot.

FIG. 8 illustrates another exemplary connector 800 that can be used in the above methods to attach the longitudinal extension to the primary construct. For example, the connector 800 can be used to attach a spinal rod of the primary construct to an elongate flexible tether or other type of extension.

The connector 800 can be substantially similar to the connector 700 described above. For example, the connector 800 can include a body 802 with a central proximal-distal axis A1, a first portion 836 that defines a tether slot 804, a second portion 840 that defines a rod slot 806, and first and second set screws 808A, 808B for securing a tether and a rod, respectively to the connector 800. The connector 800 can differ from the connector 700 in that the rod slot 806 can be open in a proximal direction such that the connector 800 has a UU-shape in a plane perpendicular to the tether axis A2 and the rod axis A3. Also, the second set screw 808B of the connector 800 can be received between the opposed arms of the second portion 840 of the connector, as opposed to a recess 734 formed in a single arm as in the connector 700. The structure and operation of the connector 800 can be otherwise the same as that of the connector 700.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While extension of a construct in a superior direction is generally described above, it will be appreciated that the systems and methods disclosed herein can also be used to extend a construct in an inferior direction, or solely within the superior and inferior limits of a primary construct, e.g., to reinforce the primary construct.

While the systems and methods disclosed herein are generally described in the context of spinal surgery with rigid spinal fixation constructs, it will be appreciated that the systems and methods herein can be used with various other types of fixation or stabilization hardware, in any bone, in non-bone tissue, or in non-living or non-tissue objects. The systems disclosed herein and the various component parts thereof can be fully implanted, or can be used as part of an external fixation or stabilization system. The systems and methods disclosed herein can be used in minimally-invasive surgery and/or open surgery.

The systems disclosed herein and the various component parts thereof can be constructed from any of a variety of known materials. Exemplary materials include those which are suitable for use in surgical applications, including metals such as stainless steel, titanium, cobalt-chromium, titanium-molybdenum, or alloys thereof, polymers such as PEEK, ceramics, carbon fiber, and so forth. The various components of the systems disclosed herein can be rigid or flexible. One or more components or portions of the system can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A surgical system, comprising:
    a primary construct having a spinal fixation rod configured to extend between an uppermost instrumented vertebra (UIV) and a lowermost instrumented vertebra (LIV);
    an extension configured to be attached to a first attachment point and a second attachment point, with the first attachment point longitudinally offset from the primary construct; and
    a monolithic connector with a first channel configured to receive the spinal fixation rod and a second channel configured to receive the extension, and at least one opening configured to receive a locking element to lock the monolithic connector to at least one of the extension or the spinal fixation rod, the at least one opening extending through a proximal surface of the monolithic connector with a longitudinal axis of the at least one opening defining a proximal-distal axis of the connector;
    wherein a terminal end of the extension is longitudinally offset from the primary construct when the extension is attached to the first attachment point and the second attachment point,
    wherein the monolithic connector is configured such that the extension is located distally of the spinal rod when the extension is received within the second channel and the spinal fixation rod is received within the first channel.

2. The system of claim 1, wherein the first attachment point is disposed superior to the UIV of the primary construct.

3. The system of claim 1, wherein the first attachment point is an implant.

4. The system of claim 1, wherein the first attachment point is an anatomical structure.

5. The system of claim 1, wherein the second attachment point is a component of the primary construct.

6. The system of claim 1, wherein the extension has a stiffness that is greater than natural patient anatomy and less than the primary construct.

7. The system of claim 1, wherein the extension is configured to restrict spinal motion to a degree that is greater than that of patient anatomy superior to the UIV of the primary construct and less than that of the primary construct.

8. The system of claim 1, wherein the extension is configured to extend along a spine of a patient from the first attachment point to the primary construct.

9. The system of claim 1, wherein the extension is configured to exert extension forces on a patient's spine.

10. The system of claim 1, wherein the extension is a polymeric tether.

11. The system of claim 1, further comprising a locking element configured to lock the monolithic connector to at least one of the extension or the spinal rod.

12. The system of claim 1, wherein the second channel of the monolithic connector further comprises a tunnel formed in a distal arm of the monolithic connector.

13. A surgical system, comprising:
    a primary construct having a spinal fixation rod configured to extend between an uppermost instrumented vertebra (UIV) and a lowermost instrumented vertebra (LIV);
    an extension configured to be attached to a first attachment point and a second attachment point, with the first attachment point longitudinally offset from the primary construct; and
    a monolithic connector with a first channel configured to receive the spinal fixation rod, a second channel configured to receive the extension, and at least one opening configured to receive a locking element to lock the monolithic connector to at least one of the extension or the spinal fixation rod, the at least one opening extending through a proximal surface of the monolithic connector with a longitudinal axis of the at least one opening defining a proximal-distal axis of the connector;
    wherein at least a portion of the second channel is formed in the monolithic connector distal to the first channel,
    wherein the second channel has a first opening in a first wall of the monolithic connector, a second opening in a second wall of the monolithic connector, and a closed tunnel formed by the monolithic connector extending therebetween.

14. The system of claim 13, wherein the first attachment point is disposed superior to the UIV of the primary construct.

15. The system of claim 13, wherein the first attachment point is an implant.

16. The system of claim 13, wherein the first attachment point is an anatomical structure.

17. The system of claim 13, wherein the second attachment point is a component of the primary construct.

18. The system of claim 13, wherein the extension has a stiffness that is greater than natural patient anatomy and less than the primary construct.

19. The system of claim 13, wherein the extension is configured to restrict spinal motion to a degree that is greater than that of patient anatomy superior to the UIV of the primary construct and less than that of the primary construct.

20. The system of claim 13, wherein the extension is configured to extend along a spine of a patient from the first attachment point to the primary construct.

* * * * *